(12) United States Patent
Dong et al.

(10) Patent No.: US 6,507,843 B1
(45) Date of Patent: Jan. 14, 2003

(54) METHOD AND APPARATUS FOR CLASSIFICATION OF DATA BY AGGREGATING EMERGING PATTERNS

(75) Inventors: Guozhu Dong, Beavercreek, OH (US); Jinyan Li, Victoria (AU); Limsoon Wong, Kuala Lumpur (MY); Xiuzhen Zhang, Victoria (AU)

(73) Assignee: Kent Ridge Digital Labs, Singapore (SG)

( * ) Notice: Subject to any disclaimer, the term of this patent is extended or adjusted under 35 U.S.C. 154(b) by 0 days.

(21) Appl. No.: 09/492,753

(22) Filed: Jan. 27, 2000

(30) Foreign Application Priority Data

Aug. 14, 1999 (SG) .............................. 9903916
Aug. 16, 1999 (SG) .............................. 9903958

(51) Int. Cl.$^7$ .............................................. G06F 17/30
(52) U.S. Cl. .................... 707/6; 707/102; 707/5; 706/50
(58) Field of Search ................ 707/6, 5, 3, 2, 707/104.1, 102, 1, 10, 101, 4, 100, 50; 706/50, 12; 705/14, 1, 26; 709/224; 435/6; 379/88.22; 600/300

(56) References Cited

U.S. PATENT DOCUMENTS 5,832,182 A  * 11/1998  Zhang et al. ................. 706/50

OTHER PUBLICATIONS

Guozhu Dong, Department of CSE, Wright State Univ. and Jinyan Li, Department of CSSE, The University of Melbourne, "Efficient Mining of Emerging Patterns Discovering Trends and Differences". Aug. 1, 1999.

\* cited by examiner

*Primary Examiner*—Sanjiv Shah
*Assistant Examiner*—Gwen Liang
(74) *Attorney, Agent, or Firm*—Nath & Associates PLLC; Harold L. Novick; Marvin C. Berkowitz

(57) ABSTRACT

Emerging patterns (EPs) are itemsets having supports that change significantly from one dataset to another. A classifier, CAEP, is disclosed using the following main ideas based on EPs: (i) Each EP can sharply differentiate the class membership of a (possibly small) fraction of instances containing the EP, due to the big difference between the EP's supports in the opposing classes; the differentiating power of the EP is defined in terms of the EP's supports and ratio, on instances containing the EP. (ii) For each instance t, by aggregating (124) the differentiating power of a fixed, automatically selected set of EPs, a score is obtained for each class (126). The scores for all classes are normalized (144) and the largest score determines t's class (146). CAEP is suitable for many applications, even those with large volumes of high dimensional data. CAEP does not depend on dimension reduction on data and is usually equally accurate on all classes even if their populations are unbalanced.

32 Claims, 3 Drawing Sheets

METHOD AND APPARATUS FOR CLASSIFICATION OF DATA BY AGGREGATING EMERGING PATTERNS

FIELD OF THE INVENTION

The present invention relates generally to database technology and more particularly to systems of data mining.

BACKGROUND

A number of systems for classifying data and performing data mining have been proposed. A number of these techniques involve decision tees, linear classification trees, and association rules. However, each of these techniques has significant disadvantages.

Conventional techniques do not handle well biased sample data which has a large volume and high dimensions. They tend to ignore weak signals. Thus, a need clearly exists for an improved system of data mining and classifying data.

SUMMARY

The aspects of the invention, Classification by Aggregating Emerging Patterns (CAEP), are directed towards a system of extracting rules in the form of emerging patterns (EP) and constructing a classifier from correctly labelled data (e.g. DNA sequences) to decide which category a sample belongs to and/or making a prediction on the sample. The system discovers features or signals that differentiate one category of data from another and builds a system to classify such data.

The system is able to nicely handle biased data that has a large volume and high dimensions. Also the system does not ignore weak signals. The EPs are associated with supports and the ratios of change in supports. The system is robust in the presence of biased sample data and is scalable in terms of large numbers of samples and in terms of dimensions in practical situations.

An EP is a signal/itemset whose supports increase significantly from one class of data to the next. In other words, it is a differentiating factor between the two classes.

The aggregation of the differentiating strengths, in terms of their supports and ratio of change, of all of some set of discovered EPs (whose cardinality is not bounded before classifier construction) that occur in a new case in a decision step is novel.

The normalization by dividing by a base score chosen at some percentile (such as 50%) across training instance of all classes is novel.

One way to find emerging pattern is based on a border-based representation of very large collections of itemsets, and processes which derive EPs by operating (such as differentials) on some borders. These borders can be first efficiently discovered using the Max-Miner technique which is scalable in terms of large number of tuples and high dimensions in practical situations.

The EPs can be used in the protein translation start-site identification problem. This is an example application of CAEP to datamining in Molecular Biology.

The CAEP classifier (i) extracts emerging patterns (EPs), (ii) uses each of these EPs as a multiple-attribute test, (iii) aggregates the power of individual EPs to get raw scores, and (iv) normalizes the raw scores by dividing them using some base scores chosen from a certain percentile of the scores of the training instances. CAEP has near equal prediction accuracy on all classes. CAEP is based on a novel border-based representation of very large collections of itemsets. It derives EPs by operating on some borders (which can also be efficiently discovered). It is scalable in terms of large number of tuples and high dimensions in practical situations.

In accordance with a first aspect of the invention, there is disclosed a method of classifying data by aggregating emerging patterns in the data using datasets for a plurality of classes using a computer processor. In the method, for each of the classes, an emerging pattern set is mined dependent upon instances of the set and opponent instances dependent upon predetermined growth rate and support thresholds. Aggregate scores of the instances are calculated for all of the classes. Base scores are then determined for each of the classes. For each test instance, the following sub-steps are performed: aggregate and normalized scores of test instance are calculated for each class; and a specified class is assigned to the test instance for which the test instance has a largest normalized score.

The method assumes the preparatory step of partitioning an original dataset into a predetermined number of datasets to form the datasets. The predetermined number of datasets is dependent upon the number of classes, Preferably, the method further includes the step of reducing the number of emerging patterns dependent upon growth rates and supports of the emerging patterns.

Preferably, the mining step includes the following steps: borders of large itemsets are determined using a large-border discovery technique; and supports and growth rates of emerging patterns are determined for the class. Optionally, the large-border discovery technique is the Max-Miner technique.

Optionally, the mining step includes the following steps: two borders of large itemsets (large borders for short) are determined of instances of the class and of the opponent class; and all emerging pattern borders are found using multiple border pairs.

In accordance with a second aspect of the invention, there is disclosed an apparatus having a computer processor for classifying data by aggregating emerging patterns in the data using datasets for a plurality of classes. The apparatus includes:

a device for, for each of the classes, mining an emerging pattern set dependent upon instances of the class and opponent instances dependent upon predetermined growth rate and support thresholds;

a device for calculating aggregate scores of the instances for all of the classes;

a device for determining base scores for each of the classes; and a device for, for each test instance, performing specified operations, the performing device including:

a device for calculating aggregate and normalized scores of test instance for each class; and a device for assigning a specified class to the test instance for which the test instance has a largest normalized score.

In accordance with a third aspect of the invention, there is disclosed a computer program product having a computer readable medium having a computer program recorded therein for classifying data by aggregating emerging patterns in the data using datasets for a plurality of classes. The computer program product includes:

a computer program source code module for, for each of the classes, mining an emerging pattern set dependent upon instances of the class and opponent instances dependent upon predetermined growth rate and support thresholds;

a computer program source code module for calculating aggregate scores of the instances for all of the classes;

a computer program source code module for determining base scores for each of the classes; and a computer program source code module for, for each test instance, performing specified operations, the computer program source code performing module includes:

a computer program source code module for calculating aggregate and normalized scores of test instance for each class, and a computer program source code module for assigning a specified class to the test instance for which the test instance has a largest normalized score.

In accordance with a fourth aspect of the invention, there is disclosed a system for extracting emerging patterns from data using a processor. The system includes:

a device for mining emerging patterns for all of a number of categories of the data;

a device for computing aggregate differentiating scores for all samples of the data and the categories; and a device for computing base scores for the categories.

Preferably, the system further includes a device for extracting the emerging patterns from the mined emerging patterns dependent upon the aggregated differentiating scores and the base scores.

Preferably, the system further includes a device for reducing the number of related emerging patterns. Two emerging patterns are related if one is a sub-pattern or subset of the other. Optionally, the system further includes a device for indicating whether the set of derived emerging patterns is to be reduced, operations of the reducing device being dependent upon the indicating device.

Optionally, the system further includes a device for reproducing in a displayable manner extracted emerging patterns. The device may print or display the extracted emerging patterns.

Optionally, the system further includes;

a device for obtaining samples from different input categories; and a device for adjustably discretizing the obtained samples.

Preferably, the system further includes a device for storing and managing the obtained samples and or the discretized samples.

Preferably, the emerging patterns are derived dependent upon one or more predetermined conditions including:

a support level threshold of a pattern in a category;

a growth rate threshold between categories;

a monotonically increasing weighting function for a growth rate; and a score specifying an aggregate differentiating score of a discretized sample and a set of emerging patterns of a category, the score being dependent upon supports and weighted growth rates of emerging patterns in a category; and a base score on the aggregate differentiating score for each category.

For a threshold on support level, the support level of a pattern (or an itemset) I in a category C is defined as $supp_c(I)$=the percentage of samples in C that exhibit that I If this threshold is not given, a default is preferably used or derived from the input data. For example, the support level threshold can be 1%.

For a threshold on growth rate, given two categories $C_a$ and $C_b$ of samples, the growth rate of a pattern (or itemset) I from $C_b$ to $C_a$ is defined as:

$$growthrate_{C_b \rightarrow C_a}(I) = \begin{cases} 0, \text{ if } supp_{C_b}(I) = 0 \text{ and } supp_{C_a}(I) = 0 \\ \text{infinity, if } supp_{C_b}(I) \text{ but not } supp_{C_a}(I) = 0 \\ \text{otherwise, } supp_{C_a}(I)/supp_{C_b}(I) \end{cases}$$

If this threshold is not given, a default can be chosen or derived from the input training data. For example, the threshold can be 5. Given a category C, its opponent category is C' which is defined to contain all instances not in category C. A pattern or itemset having a growth rate that exceeds this threshold is considered an emerging pattern from C' to C, or simply an emerging pattern of category C.

With respect to a function weight(g) for weighting growth rate g (for growth rate >1, this function should be a monotonic increasing function that takes nonnegative values. If this function is not given, a default will be chosen. For example, the function can be weight(g)=g/(g+1).

The function score(s, C) specifies the aggregate differentiating score of a sample s and a set E(C) of emerging patterns of a category C. This function involves (i) the support of emerging patterns in E(C) and (ii) weighted growth rates of emerging patterns in E(C). If this function is not given, a default will be chosen. For example, the function can be score(s, C)=sum of $supp_c$)*weight (growthrate(I)) over all pattern I that appears in s and in E(C).

The base score base_score(C) on the aggregate differentiating score for each category C can be given as a percentile of the range of aggregate differentiating scores of the training samples of that category. If this threshold is not given, a default can be chosen, for example, the 50th percentile.

An indication can be given of whether the set of derived emerging patterns should be reduced. If this indication is not given, a default decision can be made. For example, some related emerging patterns may be eliminated unless the reduction leads to poor coverage (i.e. leads to a larger number of zero scores) on training samples.

Preferably, the system further includes a device for storing and managing derived emerging patterns and the one or more conditions for deriving the emerging patterns.

Optionally, the system further includes a device for selecting patterns that cover more training samples and have stronger differentiating power, the pattern selecting device including:

a device for sorting emerging patterns between two categories into a list in decreasing order of growth rate and support;

a device for initializing a set of essential emerging patterns, essE, to contain a first emerging pattern in the list;

a device for, for each next pattern in the list, ordering the set of essential emerging patterns, the ordering device including:

a device for, for each J in the set of emerging patterns essE such that I is a sub-pattern or subset of J, replacing J by I if either of the following conditions is true:

growthrate $_{c' \rightarrow c}(I)$ exceeds growthrate $_{c' \rightarrow c}(J)$, $supp_c(I)$ greatly exceeds $supp_c(J)$ and growthrate $_{c' \rightarrow c}(I)$ exceeds the threshold on growth rate;

a device for adding I to the set of emerging patterns essE if both of the above conditions are false and I is not a super-pattern or superset of any pattern in the set of emerging patterns essE.

Preferably, the mining device includes a device for manipulating borders. Each border is an ordered pair (L, R), if each of L and R is an anti-chain collection of sets. Each element of L is a subset of an element of R, and each element of R is a superset of some element in L. A collection of sets represented by, or a set interval of, such a border are sets Y such that Y is superset of an element of L and is subset of an element of R.

Optionally, the mining device includes:

a device for determining two large borders of large itemsets in two categories having predetermined support thresholds;

a device for finding emerging pattern borders using MBD-LLBORDER processing;

a device for enumerating emerging patterns contained in found emerging pattern borders; and a device for checking through actual supports and growth rates of samples in the two categories, Given the categories C' and C of samples, the MaxMiner technique can be used to discover the two large borders of the large itemsets in C' and C having appropriate support thresholds. Then, the MBD-LLBORDER technique is used to find all the emerging pattern borders. Finally, we enumerate the emerging patterns contained in these borders, and go through samples in C' and C to check their actual supports and growth rates. Assuming that LARGE BORDER$_d$(C') and LARGERBORDER$_r$(C) have been found for some d and r satisfying t=p*d, where p is an appropriate threshold on growth rate, the MBD-LLBORDER technique is used to find all emerging patterns such that their supports in C exceed d*p but their supports in C' are less than d. The MBD-LLBORDER technique is as follows:

Let LAGEBORDBR$_d$(C') be ($\{\{\ \}\}, \{C_1, C_2, \ldots, C_m\}$)
Let LARGERBORDER$_r$(C) be ($\{\{\ \}\}, \{D_1, D_2, \ldots, D_n\}$)
MBD-LLBORDER(LAGEBORDE$_n$(C'), LARGEBORDER$_r$(C)
EPBORDERS<Θ{ });
for j from 1 to n do
   if some $C_I$ is superset of $D_J$ then continue;
   $\{C_I', \ldots, C_m'\} \Theta \{(C_I \text{ intersect } D_j, \ldots C_m \text{ intersect } D_j\}$;
   RIGHTBOUNDΘthe set of all maximal itemsets in $\{C_I', \ldots, C_m'\}$;
   add BORDER-DIFF(($\{\{\ \}\}$, $D_j$), ($\{\{\ \}\}$, RIGHTBOUND)) into EPBORDERS
return EPBORDERS;

The function BORDER-DIFF is employed to derived differentials between a pair of borders of special forms: Given a pair of borders ($\{\{\ \}\}$, $\{U\}$) and ($\{\{\ \}\}$,R), BORDER-DIFF derives another border (L, $\{U\}$) such that the collection of sets represented is exactly those sets represented by ($\{\{\ \}\}$, $\{U\}$) but not represented by ($\{\{\ \}\}$, R). Importantly, BORDER-DIFF achieves this by manipulating only the itemsets in the borders:

BORDER-DIFF(($\{\{\ \}\}$, $\{U\}$), ($\{\{\ \}\}$, $\{S_1, \ldots, S_k\}$))

--- initialize L to $\{\{x\} \times \text{ in } U-S_1\}$;
   for i from2 to k do
        L ← $\{X \text{ union } \{x\}[X] \text{ in L, x in } U-S_1\}$;
        remove all itemsets Y in L that are not minimal;
   return (L $\{U\}$);

---

In accordance with a fifth aspect of the invention, there is disclosed a system for classifying data using a processor. The system includes:

a device for inputting samples of the data to be classified;

a device for mining emerging patterns for all of a number of categories of the data;

a device for computing aggregate differentiating scores for all samples of the data and the categories;

a device for computing base scores of aggregate differentiating scores for all samples and categories; and a device for assigning a category to each sample, the category assigned to a sample having a normalized score that is maximal for the sample.

Preferably, the system further includes a device for outputting classification decisions on the samples.

In accordance with a sixth aspect of the invention, there is disclosed a system for ranking and classifying data using a processor. The system includes:

a device for inputting samples of the data to be classified;

a device for mining emerging patterns for all of a number of categories of the data;

a device for computing aggregate differentiating scores for all samples of the data and the categories;

a device for computing base scores of aggregate differentiating scores for all samples and categories; and a device for ranking each category against each sample by measuring a normalized score for the sample, where the greater a normalized score, the higher is the rank of the category for the sample, the normalized score with respect to a category is formed by dividing the aggregate differentiating score by a corresponding base score.

Preferably, the system further includes a device for outputting ranked classification decisions on the samples.

BRIEF DESCRIPTION OF THE DRAWINGS

In the following description, embodiments of the invention are described with reference to the drawings, in which.

DETAILED DESCRIPTION

Figure 1:
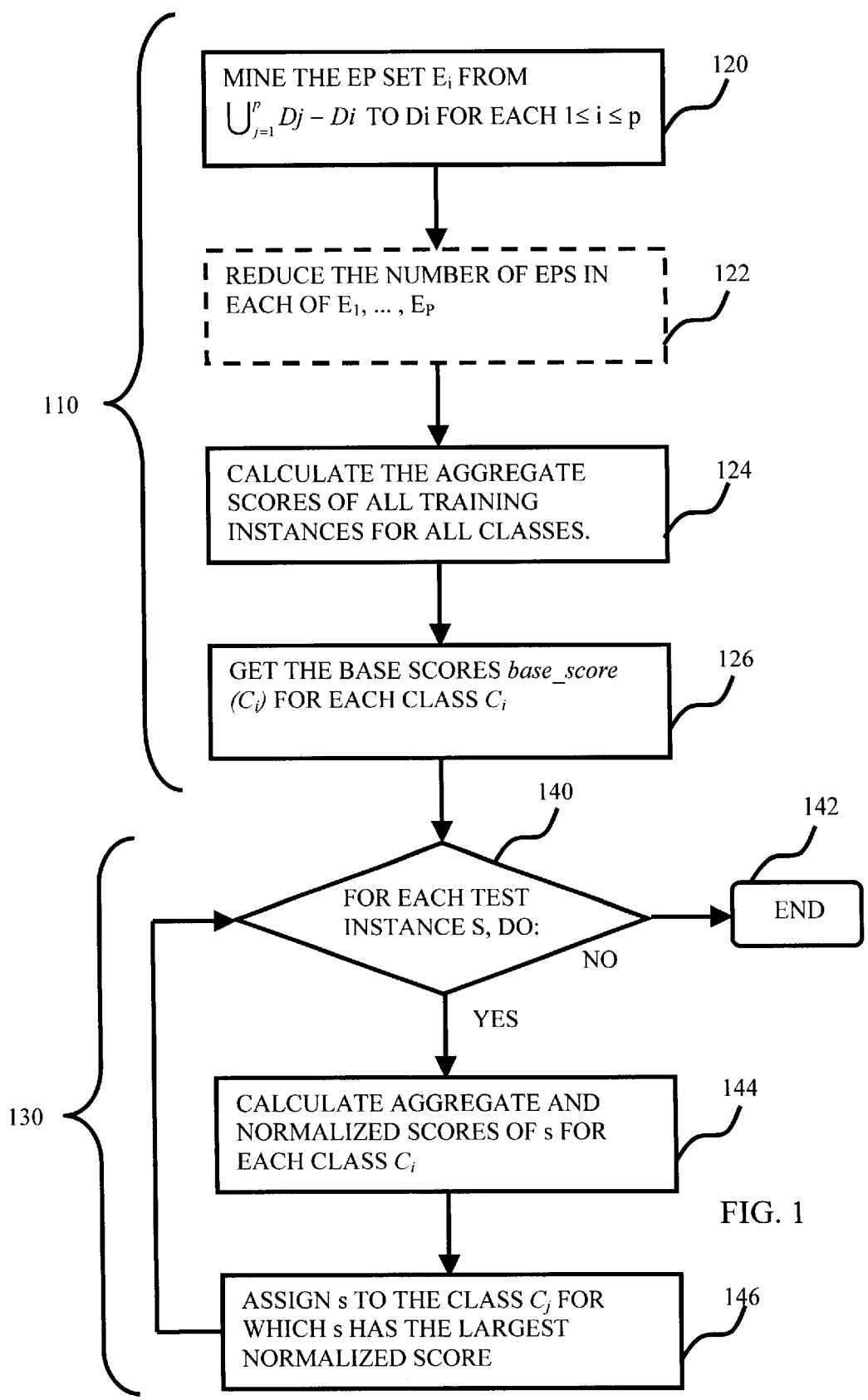
FIG. 1 is flow diagram of the process of classification by aggregating emerging patterns in accordance with a first embodiment of the invention, where $D_j$ is the set of samples of the jth class.

A method, an apparatus, and a computer program product for classification of data by aggregating emerging patterns (EP) are described. In the following description, numerous details are set forth. It will be apparent to one skilled in the art, however, that the present invention may be practised without these specific details. In other instances, well-known features are not described in detail so as not to obscure the present invention.

The detailed description is organised as follows:

1. Introduction
2. Emerging Patterns and Preliminaries
3. Classification by Aggregating EPs
4. Efficient Mining of EPs
5. Reduction of EPs Used
6. Selection of Thresholds and Base Scores
7. Rice-DNA, Sensitivity and Precision 8. Experimental Results
9. Computer Implementation

1. Introduction

The embodiments of the invention provide a new classifier, Classification by Aggregating Emerging Patterns (CAEP), which is suitable for many applications, even those with large volumes of high dimensional data. The classifier is highly accurate and is usually equally accurate on all classes even if their populations are unbalanced. These advantages are achieved without dimension reduction on data The two principal ideas behind CAEP are:

(i) Emerging patterns (EPs) are used to build the CAEP classifier. Such EPs are described by and incorporated herein by cross-reference to Dong, Guozhu, and Li, Jinyan, "Efficient mining of emerging patterns: Discovering trends and differences", ACM SIGKDD 1999 International Conference on Knowledge Discovery & Data Mining, AUG. 15–18, 1999, San Diego, USA pages 43–52, Roughly speaking, EPs are itemsets having supports (i.e. frequencies) that increase significantly from one class of data to another. For example, the itemset {odor=none, stalk-surface-below-ring=smooth, ring-number=one} in the Mushroom dataset is a typical BP, whose support increases from 0.2% in the poisonous class to 57.6% in the edible class, at a growth rate of 288

$$\left( = \frac{57.6\%}{0.2\%} \right).$$

The Mushroom dataset is disclosed by Lincoff, Gary, "The Audubon Society field guide to North American mushrooms", Knopf, New York, 1981. Here, an item is a simple test on an attribute, and an EP is a multi-attribute test. Each EP can have a strong power to differentiate the class membership of some instances. Indeed, if a new instance s contains the above EP, then with odds of 99.6% s can be claimed to belong to the edible class. In general, the differentiating power of an EP is roughly proportional to the growth rate of the EP's supports and the EP's support in the target class.

(ii) An individual EP is usually sharp in telling the class of only a very small fraction (e.g. 3%) of all instances. Thus, the EP has poor overall classification accuracy if the EP is used by itself on all instances. To build an accurate classifier, for each class C, all the EPs meeting some support and growth rate thresholds from the (opponent) set of all non-C instances, are found. Then, the power of the discovered EPs for classifying an instance s are aggregated using the following steps: Derive an aggregate differentiating score for each class C, by summing the differentiating power of all EPs of C that occur in s; and normalize the score for C by dividing the score by a base score (e.g. median) of the training instances of C. Finally, let the largest normalized score determine the winning class. Normalization is done to reduce the effect of unbalanced distribution of EPs among the classes as classes with more EPs frequently give higher scores to instances, even to those from other classes.

CAEP achieves good predictive accuracy on all the datasets tested. The CAEP classifier gives better accuracy than conventional classifiers such as C4.5 and CBA. The high accuracy is achieved because a high dimensional method is used to solve a high dimensional problem: each EP is a multi-attribute test and the CAEP classifier uses the combined power of an unbounded set of EPs to arrive at a classification decision. Being equally accurate in all classes is useful for many applications, where there are a dominant class (e.g. 98% of all instances) and a minority class, and the sole purpose of classification is to accurately catch instances of the minority class. Classification accuracy is not the desired measure in such a situation, because the classifier which classifies all instances as in the dominant class would be mistakenly considered a good classifier. In the following description, classifiers are measured using sensitivity and precision, which reward classifiers that correctly label more minority instances and do not mislabel many other instances.

The CAEP classifier can be efficiently built for large, high-dimensional training datasets in a scalable way, since EPs can be discovered efficiently using border-based techniques and the Max-Miner technique. CAEP classifiers can quickly be produced for datasets such as the Mushroom dataset, whose records consist of 21 attributes.

Several parameters need to be selected. This is done automatically using the performance of the resulting classifier on the training instances as guidance. Because of the use of aggregation (and normalization), the traditional overfitting problem has not been encountered in experiments.

CAEP is fundamentally different from previous classifiers in use of a new knowledge type in the form of EPs. To arrive at a score for decision making, CAEP uses a set of multi-attribute tests (EPs) for each class. Most conventional classifiers consider only one test on one attribute at a time; while a few exceptions, consider only one multi-attribute test to make a decision.

Aggregation of the differentiating power of EPs is different from bagging or boosting as described in Schapire, R F, "The Strength of Weak Learnability", *Machine Learning*, 5(2), 1990, pp. 197–227, which manipulate the training data to generate different classifiers and then aggregate the votes of several classifiers. With CAEP, each EP is too weak as a classifier and all the EPs are more easily obtained.

Loosely speaking, aggregation of the power of EPs in classification is related to the Bayesian prediction theory. For an instance t viewed as an itemset, Bayesian prediction labels t as $C_k$, where the probability $\Pr(t|C_k)*\Pr(C_k)$ is the largest among the classes. The optimal Bayesian classifier needs to "know" the probability $\Pr(t|C_k)$ for all possible t, which is clearly impractical for high dimensional datasets. Roughly speaking, CAEP "approximates" $\Pr(t|C_k)*\Pr(C_k)$ using a normalized score.

2. Emerging Patterns and Preliminaries

Original data instances are assumed to have m attribute values. formally, a data instance having m attribute values is just a list of pairs of the form $l_i=v_i$, where $l_i$ is a symbol (usually a character string) called the attribute name and $v_i$ is a symbol (usually a number or a Boolean/binary) called the attribute value. When the ordering of the attributes are fixed, the $l_i$'s are usually omitted. When the attributes are all Boolean-valued, only those $l_i$'s whose corresponding $v_i$'s are true (ie. have value 1) are listed; a particularly convenient convention to represent such a data instance is to list the indices of those $v_i$'s that are true; for example, if $v_1$, $v_2$ and $V_3$ are the only attribute values that are true in a data instance, we can represent this data instance as {1, 2, 3}. Each instance in the training dataset D is associated with a class label, out of a total of p class labels: $C_1, C_2, \ldots, C_p$. The dataset D is partitioned into p sets, $D_1, D_2 \ldots D_p$, with $D_i$ containing all instances of class $C_i$.

Emerging patterns are defined for binary transaction databases. To find them, a raw dataset is encoded into a binary one: The value range of each continuous attribute is discretized into intervals. Each (attribute, interval) pair is called an item in the binary (transaction) database, which is represented as an integer for convenience. An instance t in the raw dataset is then mapped to a Faction of the binary database: t has the value 1 on exactly those items (A, v) where t's A-value is in the interval v. This new t is represented the set of items for which t takes 1. Henceforth, the datasets $D_1, D_2 \ldots D_p$ are assumed to be binary.

Let I be the set of all items in the encoding. An itemset X is a subset of I, and X's support in a dataset D', $supp_{D'}(X)$, is $$\frac{|\{t \in D' \mid X \subseteq t\}|}{|D'|}.$$

Given two datasets D' and D", the growth rate of an itemset X from D' to D" is defined as growth_rate$_{D' \to D''}$(X)=SUPP$_{D''}$(X)/Supp$_{D'}$(X), if supp$_{D'}$(X) is not 0;

growth_rate$_{D' \to D''}$(X)=0 if Supp$_{D'}$(X)=Supp$_{D''}$(X)=0; and growth rate$_{D' \to D''}$(X)=infinity, if Supp$_{D'}$(X)=0 and Supp$_{D''}$(X) is not zero.

Emerging patterns are itemsets with large growth rates from D' to D".

Definition 1. Given D', D" and a growth rate threshold $\rho>1$, an emerging pattern ($\rho$-EP or simply EP)from D' to D" is an itemset e where growth rate$_{D' \to D''}$(e)$\geq \rho$.

Example 1. Consider the following training dataset with two classes, P and N

TABLE 1

| P | N |
|---|---|
| {2, 6, 7, 10} {3, 5, 7, 10} {3, 4, 8, 10} | {1, 6, 7, 10} {1, 6, 7, 9} |
| {2, 4, 8, 9} {1, 4, 8, 10} {3, 5, 8, 10} | {3, 4, 8, 9} {1, 5, 7, 10} |
| {1, 5, 8, 9} {2, 5, 7, 9} {2, 6, 8, 10} | {3, 5, 7, 9} |

Then {1, 9} is an EP from class P to class N with a growth rate;

$$\frac{9}{5};$$

it is also an $\rho$-EP for any $1 \leq \rho \leq$ $$1 < \rho \leq \frac{9}{5}.$$

Some other EPs are given later.

3. Classification by Aggregating EPs

The major ideas and components of the CAEP classifier are described hereinafter: (1) how to partition the dataset to derive the EPs for use in CAEP, (2) how individual EPs can differentiate class memberships, (3) how to combine the contribution of individual EPs to derive the aggregate scores, and (4) how to normalize the aggregate scores for deciding class membership. An overview is also given on how to construct and use CAEP 3.1 Partitioning Dataset to got FPs of Classes For each class $C_k$, a set of EPs is used to contrast the class'instances, $D_k$, against all other instances: let $D'_k=D'-D_k$ be the opposing class, or simply the opponent, of $D_k$. The EPs are then mined from $D'_k$ to $D_k$. These EPs are referred to as the EPs of class $C_k$, and sometimes refer to $C_k$ as the target class of these EPs.

For Example 1, some EPs of class N (i.e. from P to N are (e: {1}, supp$_N$ (e):0.6, growth_rate $_{P \to N}$: 2.7), ({1, 7}, 0.6,∞), ({1, 10}, 0.4, 3, 6), ({3, 4, 8, 9}, 0.2, ∞). Similarly, some EPs of P are ({2}, 0.44, ∞), ({8}, 0.67, 3.33) and ({4, 8}, 0.33, 1.67).

3.2 Differentiating Power of Individual EPs

Each EP can sharply differentiate the class membership of a fraction of instances containing the EP. This sharp differentiating power is derived from the significant difference between the EP's supports in the opposing classes. Continuing with Example 1, consider the EP({1, 10}, 0.40, 3.60) for class N. Suppose s is an instance containing this EP. The next determination to be made are the odds that s belongs to N, given that s contains this EP. To simplify the discussion, all classes are assumed have roughly equal population counts, then the answer is $$\frac{supp_N}{supp_N + supp_P} = \frac{3.60 * supp_P}{360 * supp_P + supp_P} = \frac{3.60}{3.60 + 1} = 78\%,$$

since $supp_N = 360 * supp_P$.

Without this assumption, supports (e.g. Supp$_N$) need to be replaced by counts (e.g. supp$_N$*count$_N$, where count$_N$ is the number of instances of class N), and similar odds can be obtained. Observe that this EP has no differentiating power on instances s' that do not contain the EP. Therefore, assuming the population ratio in the training data accurately reflects the ratio in test instances and all classes have roughly equal population counts, this EP cane used to differentiate the class membership with the probability of 78% for roughly $$\frac{supp_N + supp_P}{2} = 0.5 * \left(1 + \frac{1}{3.60}\right) * supp_N = 25\%$$

of the total population.

The fraction of instances which contain an EP may be a small fraction (25% above, but much smaller, e.g. 3%, in many examples) of all instances. Hence, the EP cannot yield very accurate predictions if it is used by itself on all instances. For example, if the above EP is applied on all instances, an overall predictive accuracy of roughly 0.25*0.78=19.5% would be arrived at. This would be much lower if coverage is only 3%.

3.3 Better Overall Accuracy by Aggregated Score

A single EP is sharp on predicting class membership of a small fraction of instances, but not on all instances. The combining of the strength of a set of EPs is shown in order to produce a classifier with adequate overall accuracy.

Roughly speaking, given a test instance s, all the EPs of a class $C_i$ that s contains contribute to the final decision of whether s should be labelled as $C_i$. This gives an advantage of covering more cases than each single EP can cover, because different EPs complement each other in their applicable populations. To illustrate, consider Example 1. The largest fraction of a population that a single EP (e.g. {8}) can cover is around 50%, whereas the seven EPs given under heading 3.1 have a much larger combined coverage, around $$\frac{12}{14} = 85.7\%.$$

The manner of combining the differentiating power of a set of EPs is now described. A natural way is to sum the contributions of the individual EPs. Other possibilities can be practiced. Regarding how the contribution of a single EP is formulated roughly, a product is used of the odds discussed earlier and the faction of the population of the class that contain the EP. More specifically, let e be an EP of class C, e's contribution is given by $$\frac{\text{growth\_rate}(e)}{\text{growth\_rate}(e)+1} * supp_C(e).$$

Observe that the first term is roughly the conditional probability that an instance is in class C given that the instance contains this EP e, and the second term is the fraction of the instances of class C that this EP applies. The contribution is proportional to both growth_rate(e) and $supp_c(e)$. The scores of instances for the classes are now defined.

Definition 2. Given an instance s and a set E(C) of EPs of a class C discovered from the training data, the aggregate score (or score) of s for C is defined as $$\text{score}(s, C) = \sum_{e \subseteq s, e \in E(c)} \frac{\text{growth\_rate}(e)}{\text{growth\_rate}(e)+1} * supp_C(e).$$

The calculation of contributions of EPs and scores of instances is illustrated using Example 1 and the instance s={1, 5, 7, 9}. Among EPs of the growth rate threshold of 1.1, s contains 2 of class P: ({15}, 44%, 1.11), ({1, 5, 9}, 11%, ∞); s contains 10 of class N: ({1}, 60%, 2.7), ({7}, 80%, 2.4), ({1, 5}, 20%, 1.8), ({1, 7}, 60%, ∞), ({1, 9}, 20%, 1.8), ({5, 7}, 40%, 1.8), ({7, 9}, 40%, 3.6), ({1, 5, 7}, 20%, ∞), ({1, 7, 9}, 20%, ∞), ({5, 7, 9}, 20%, 1.8). The aggregate score of s for P is:

$$\text{score}(s, P) = \frac{1.11}{1.11+1} * 0.44 + \frac{\infty}{\infty+1} * 0.11 = 0.52 * 0.44 + 1 * 0.11 = 0.33.$$

Similarly, the contributions of the 10 EPs for N are respectively 0.41, 0.56, 0.12, 0.60, 0.12, 0.24, 0.31, 0.20, 0.20, 0.12, and their sum is score (s, N)=2.88.

3.4 Normalizing the Scores to Make a Decision

For each instance s, the method of using the scores for all classes to predict its class is now described.

One might be tempted to assign to s the class label C. for which the score of s is the largest. This turns out to be an undesirable strategy. The main reason for this is that the number of EPs for different classes may not be balanced, which is a frequent scenario for applications where some classes may have more random (uniform) distributions of values and consequently fewer EPs. If a class C has many more EPs than another class C', then instances usually get higher scores for C than for C', even for training instances of class C'. This indeed happens, for example in the rice-DNA dataset described hereinafter under heading 6, which consists of a positive class and a negative class. The negative class contains mostly "random" instances. The ratio of the number of EPs of the positive to that of the negative is 28:1 when the threshold is 3% and the growth rate threshold is 2.

In the embodiments of the invention, this problem is solved by normalizing the scores, i.e. by dividing the scores using a score at a fixed percentile for the training instances of each class. More specifically, a base score for each class C, base_score(C), is first found from the training instances of the class. The normalized score of an instance s for C, norm_score (s, C), is defined as the ratio score (s, C)/base_ score (C). Observe that the use of the term "normalized" in this context is a slight abuse, since the normalized scores may be >1. Instead of letting the class with the highest raw score win, the class with the largest normalized score wins. A tie is broken by letting the class with the largest population win.

To determine the base scores, base_score(C) is the median of the scores of the training instances class C; that is, exactly 50% of the training instances of C have scores larger than or equal to base_score(C), Fifty percent (50%) does not have to be used in fact, other percentiles between 50%–85% give roughly similar results. The CAEP construction process automatically chooses a good percentile in this range, by testing the performance of the constructed classifier on the training instances. Percentages on the two extreme ends (e.g. 3%) are not used, because the training instances usually contain some outliers. If such a choice is used, the outliers give too much influence.

Example 2. For a simple illustration of the decision process, assume there are 5 training instances from each of the positive (+ve) and negative (−ve) classes, and their scores are given in Table 2:

TABLE 2

| +ve training instances | | −ve training instances | |
|---|---|---|---|
| score(s, +ve) | score(s, −ve) | score(s, +ve) | score(s, −ve) |
| 18.44 | 0.31 | 4.89 | 5.51 |
| 16.65 | 0.39 | 8.37 | 5.47 |
| 15.76* | 0.05 | 2.8 | 5.4* |
| 15.28 | 0.21 | 9.93 | 4.97 |
| 14.52 | 0.41 | 10.31 | 4.8 |

The (median) base scores for the positive and negative classes of Table 2 are respectively 15.76 and 5.4. Given a test instance s (known to be from the negative class) with scores 7.07 and 4.82 for the positive and negative classes respectively, the following results:

norm_score(s,+ve)=7.07/15.76=0.45
norm_score(s,−ve)=4.82/5.4=0.89 s is thus labelled as negative. Observe that this decision is made even when s has a higher raw score for the positive class.

3.5 The Entire Process

The entire process for building and using CAEP is illustrated in FIG. 1 and described below, assuming that the original dataset is partitioned according to the class labels.

CAEP (training datasets $D_1, \ldots D_p$ for p classes $C_1, \ldots, C_p$)

training phase (110)

In step 120, mine the EP set $E_i$ from $U^p_{j=1} D_j - D_i$ to $D_i$ for each 1≦i≦p; ;; A growth rate threshold is given, or set to a default e.g. 2

In step 122, optionally (indicated by dashed lines), reduce the number of EPs in each of $E_l, \ldots, E_p$;

In step 124, calculate the aggregate scores of all training instances for all classes;

In step 126, get the base scores base_score($C_1$) for each class $C_i$; ;; resting phase (130)

In decision block 140, for each test instance s (YES) do:

In step 144, calculate aggregate and normalize scores of s for each class $C_i$;

In step 146, assign to s the class $C_j$ for which s has the largest normalized score.

The process of FIG. 1 is grouped into two phases: training phase 110 and testing phase 130. The training phase 110 includes steps 120, 124, and 126, and optionally includes step 122. The testing phase 130 includes decision block 140 (for loop) and steps 144, 146, and 142. When all instances s have been processed (decision block 140 returns false (NO), processing terminates in step 142.

4. Efficient Mining of EPs

For the discovery of EPs, mining methods used are introduced by Dong, Guozhu, and Li, Jinyan, "Efficient mining of emerging patterns: Discovery trends and differences" in ACM SIGKDD 1999 International Conference on Knowledge Discovering and Data Mining, Aug. 15–18, 1999, San Diego, USA, pages 43–52. A key tool used by those efficient methods is that of borders, useful for the concise representation and efficient manipulation of large collections of itemsets. This technique is set forth in Appendix B.

Example 3. An example border is <L={{22}, {57}, {61}}, R={{22 34, 36, 57, 61, 81, 85, 88}}>. The collection of itemsets represented by this border is $\{Y \mid \exists X \in L, \exists Z \in R$ such that $X \subseteq Y \subseteq Z\}$. Representative itemsets covered in the border include {22}, {22, 57}, {36, 57, 81, 88}. This is actually a border for the EPs from the edible to the poisonous class, of an encoding of the Mushroom dataset, at support threshold a δ=40% in the poisonous and growth rate threshold ρ=2.

To calculate the aggregate score contributed by all the EPs (meeting some thresholds) of a class $C_i$, the following must be done: (i) find the EPs of $C_i$ and (ii) discover those EP's supports and growth rates. Two methods can be used to do this.

1. The large-border based approach: The Max-Miner technique of Appendix 1 is first used to efficiently discover the border of the large itemsets from $D_i$. Such a border is called a large border, hence the word "large" in the title of this approach. If the large itemsets represented by the border can be enumerated in memory, then with one more scan of $D_i$ and $D_i'$, the supports and growth rates of the EPs of $C_i$ can be obtained. If this approach can be applied, all EPs can be discovered whose supports in $D_i$ are larger than the given support threshold. However, because some larger borders may represent "exponentially" many candidate itemsets, only a small portion of these candidates can be held in memory. If so, the next approach can be used.

2. The border differential based approach: The Max-Miner technique is used to discover the two large borders of the large itemsets in $D_i$ and the opponent $D_i'$ having certain support thresholds. Then the MBD-LLborder (multiple-border differential) process of Dong, Guozhu, and Li, linyan, "Efficient mining of emerging patterns: Discovery trends and differences," ACM SIGKDD 1999 Int'l Conf. On Knowledge Discovery and Data Mining, AUG. 15–18, 1999, San Diego, USA, pp. 43–52, extracted in Appendix 2, to find all the EP borders. Finally, the EPs contained in the EP borders are encountered, and $D_i$ and $D_i'$ are checked for their supports and growth rates. With 13 EP borders of the Mushroom dataset for some support thresholds, using this approach, the supports and growth rates of 4692 EPs can be quickly found. Since the MBD-LLborder process only finds EPs whose supports in the second dataset are ≧one support threshold and in the first dataset are <another support threshold, this method is applied multiple times on multiple pairs of large borders, or this method is combined with above approach 1 to get the important EPs satisfying the given support and growth rate thresholds.

Reduction of EPs Used

Given a class C, it is desired to find as many EPs as possible to give good coverage of the training instances. At the same time, EPs are preferred that have relatively large supports and growth rates, as these characteristics correspond to larger coverage and stronger differentiating power. Often, many of the EPs can be removed without loss of too much accuracy, by exploiting relationships between the EPs. Reduction can increase understandability of the classifier and may even increase predictive accuracy.

The reduction step is optional. This step should not be done if the step leads to poor classification of the training instances. This is a training time decision.

The method to reduce the number of EPs uses these factors: the absolute strength of EPs, the relationships between EPs, and the relative difference between their supports and growth rates. The absolute strength of EPs is measured using a new growth rate threshold ρ', which should be larger than the growth rate threshold p for the EPs. The main idea is to select the strong EPs and remove the weaker EPs, which have strong close relatives. The selected EPs are referred to as the essential EPs.

To reduce the set of EPs, the mined EPs are sorted first into a list E, in decreasing order on (growth-rate, support). The set of essential EPs, essE, is initialized to contain the first EP in E. For each next EP e in E, step 1 and then step 2 are performed:

1. For each EP x in essE such that e [S1]⊂, replace x by e if 1.a or 1.b is true:
   1.a. growth_rate(e)≧growth_rate(x)
   1.b. supp(e)>>supp(x) and growth_rate(e)≧p'
2. Add e to essE if both 1.a and 1.b are false, and e is not a superset of any x in essE.

EPs are selected in this way because: When condition 1.a is true, e definitely covers more instances than x since e ⊂ x, and e has a stronger differentiating power than x because e has a higher growth rate. A typical situation captured by condition 1.b is when x is an EP with growth rate but a very small support, whereas e is an EP having a growth rate that is less than that of x but e has a much larger support than x. In this case, e is preferred since e covers many more cases than x and has a relatively high differentiating power already due to e's growth rate being larger than p'. To illustrate this point, consider these two EPs of the Iris-versicolor class from the classical Iris dataset of R. A. Fisher described in Fisher, R. A. "The use of multiple measurements in taxonomic problems" Annual Eugenics, 7, Part II, 179–188 (1936); also in "Contributions to Mathematical Statistics" (John Wiley, NY. 1950).

$e_1$=({1, 5, 11}, 3%, ∞)
$e_2$=({11}, 100%, 22.25)

The EP $e_2$ is clearly more useful than $e_1$ for classification, since $e_2$ covers 32 times more instances and $e_2$'s associated odds, 95.7%, is also very near that of the other EP, $e_1$. In experiments, for 1.b, the default value of p' was set to 20 and the default interpretation of the condition "supp(e) >>supp (x)" is $$\frac{supp(e)}{sipp(x)} \geq 30.$$

These parameters can be tuned based on coverage on training instances.

6. Selection of Thresholds and Base Scores

To build a classifier from a training dataset, two thresholds (one for support and one for support growth rate) and a base score for each class need to be selected.

The selection of the thresholds and base score can be done automatically with the guidance of the training data: Processing starts with default thresholds and percentiles for the base scores. Then a classifier is built and the classifier's performance on the training instances is found. The classifier building process tries several alternatives and sees if significant improvements are made. The best choice is then selected.

From experiments, it is observed that the lower the support threshold δ, the higher the predictive accuracy the classifier achieves; and for each support threshold, the higher the growth rate threshold, the higher predictive accuracy the classifier achieves. Once δ is lowered to 1%–3%, the classifier usually becomes stable in predictive accuracy. If the growth rate threshold is then raised to the highest possible (described hereinafter), CAEP typically has better predictive accuracy than conventional techniques like C4.5 and CBA. In the experiments reported hereinafter, δ is between 1%–3%. The exact choice of δ is influenced by the how much running time is allowed for CAEP construction.

The growth rate threshold also has strong effect on the quality of the classifier produced The general principle adopted is to (a) mine EPs with a small initial growth rate threshold such as 2, and (b) automatically select a larger final growth rate threshold guided by the coverage of selected EPs on the training instances. Generally, if the growth rate threshold is too high, the classifier contains too few EPs and the classifier may have low accuracy because of poor coverage of the training instances. Coverage of a set of EPs is measured by the number of zero scores produced on the training instances: the fewer the number of zero scores the better the coverage. On the other hand, if the growth rate threshold can be raised without lowering the coverage of training instances, then raising the growth rate threshold typically results in a classifier with higher predictive accuracy. Experiments show that with support threshold 1%–3%, the UCI datasets usually yield a huge number of EPs with growth rates from 1 to ∞(Rice-DNA data is an exception, described hereinafter under heading). The automatically chosen growth rate threshold is usually around 15.

7. Rice-DNA, Sensitivity and Precision

A motivation for more accurate measure of classifiers comes from a rice-DNA dataset containing rice-DNA Kozak sequences.

A genomic DNA is a string over the alphabet of {A, C, T, G}. The context surrounding the protein translation start site of a gene is called the Kozak sequence described in Kozak, Mary, "An analysis of 5'—noncoding sequences from 699 vertebrate messenger RNAs, *Nucleic Acids Research*, 15:8125–8148, 1987.

Correct identification of such start sites from a long genomic DNA sequence can save a lot of labor and money in identifying genes on that sequence. The start site is always the A-T-G sequence. The context surrounding the A-T-G has been the most important information to distinguish real start sites from non-start sites. A context is typically taken from up to 15 bases up stream of A-T-G to 10 bases down stream. So a Kozak sequence—for the purposes herein—consists of 25 letters (excluding the A-T-G).

In the genomic DNA sequences, non-start sites (negative) overwhelm real start sites (positive) typically at a ratio of 24:1 or more. So a distinctive feature of the rice-DNA dataset is that the number of instances of the two datasets are significantly unbalanced. What makes the treatment of this dataset more difficult is that the number of positives, which is more important in reality, is far more the minority. With this very unbalanced dataset, even the just-say-no classifier, which always predicts an instance to be negative, will have an overall accuracy of $$\frac{24}{25} = 96\%.$$

Unfortunately, the fact is that not a single real start site has been identified, which is against the aim of classification in the embodiments of the invention.

From this analysis, it can be seen that in evaluating a classification method more meaningful measures than accuracy or error rate on the whole dataset are desirable. A measure is used in terms of two parameters, namely sensitivity and precision, for each class, which have long been used in the signals world and in information retrieval.

Definition 3. Given N instances whose class is known to be C, for a classifier P. if P labels N' instances as of class C. of which $N_1$ are indeed to be of class C, then $N_1/N$ is called P's sensitivity on C, denoted sens(C), and $N_1/N'$ is called P's precision on C, denoted prec(C). For the special case of N'=0, we define sens(C)=0, prec(C)=0.

From the above definition, it can be seen that sensitivity on a class C is an indication of the strength of a classifier on C and precision tells how much confidence the classifier has on C. Using the "minority" vs "majority" terminology, sensitivity for the minority class represents the percentage of the minorities caught by the classifier, precision for the minority class represents the percentage of those claimed to be of the minority class are indeed in the minority class. Clearly, these are a more accurate description of the performance of the classifier on class C.

Example 4. Given the ratio of negative to positive instances of 24: 1, the performance of the just-say-no classifier on the rice-DNA dataset can be examined:

$$sens(-ve) = \frac{24}{24} = 100\% \cdot prec(-ve) = \frac{24}{25} = 96\%$$

Since the sensitivity and precision on the positive class are more important for the rice-DNA dataset, it can be concluded that the just-say-no classifier performs poorly on the rice-DNA dataset and better classifiers should be sought.

8. Experimental Results

The CAEP method compares with favourably classifiers C4.5 and CBA. Except for rice-DNA, the datasets used are from the UCI machine learning repository disclosed in Murphy, P. M., and Aha, D. W., "UCI repository of machine learning data base", URL=http://www.ics.uci.edu/~mlearn/MLRepository.html. Furthermore, CAEP is tested on some datasets with a large number of records and where each record is long, where no results of C4.5 or CBA are known.

Discretization of continuous attributes can be done by an entropy method or by an "equal bin population" method. One implementation of the equal bin population method is as follows: For each attribute, we first obtain the count of occurrences of each value in the training instances; then each value v is mapped to an interval [0.5*(v+vl), 0.5*(v+vr)), where vl is the largest among all values that are less than v, and vr is the smallest among all values that are larger than v; then iteratively we combine a consecutive pair of intervals which when combined give the smallest (in terms of number of occurrences in instances) new combined interval. All the results are obtained by 10-fold cross validation.

Table 3 compares the overall predictive accuracy of CAEP (without reduction), C4.5 (without discretization) and CBA. Dashes indicate that results are unavailable.

Columns 2, 3 and 4 describe the datasets: the numbers of records, attributes and classes respectively. Rice-DNA and Mushroom are the most challenging datasets, having both a large number of instances and high dimensionality. Observe that datasets of 2, 3 and even more classes are included, and that CAEP performs equally well. Columns 5, 6, and 7 give the average predictive accuracy of C4.5, CBA, and CAEP over 10-fold cross-validation

TABLE 3

Accuracy Comparison

| Dataset | # records | # attributes | # classes | C4.5 | CBA | CAEP |
|---|---|---|---|---|---|---|
| Australian | 690 | 14 | 2 | 84.28% | 85.51% | 86.21% |
| German | 999 | 20 | 2 | 71.70% | 73.20% | 72.50% |
| Heart | 270 | 13 | 2 | 76.69% | 81.87% | 83.70% |
| Pima | 768 | 8 | 2 | 71.10% | 73.03% | 75.00% |
| Vehicle | 846 | 18 | 4 | 69.82% | 68.78% | 66.32% |
| Waveform | 5000 | 21 | 3 | 70.40% | 75.34% | 84.68% |
| Breast | 699 | 10 | 2 | 95.42% | 95.28% | 97.28% |
| Cleve | 303 | 13 | 2 | 72.29% | 77.24% | 83.25% |
| Hepatitis | 155 | 19 | 2 | 80.00% | 80.20% | 83.03% |
| Wine | 178 | 13 | 3 | 92.70% | 91.60% | 97.11% |
| Ionosphere | 351 | 34 | 2 | 90.00% | 91.80% | 90.04% |
| Iris | 150 | 4 | 3 | 95.30% | 92.90% | 94.67% |
| Tic-tac-toe | 958 | 9 | 2 | 99.40% | 100.00% | 99.06% |
| Rice-DNA | 15760 | 25 | 2 | — | 55.30% | 70.87% |
| Mushroom | 8124 | 22 | 2 | — | — | 98.82% |

Table 4 shows the accuracy of CAEP, before and after reduction on several datasets. It can be seen that although the number of EPs has been diamatically reduced after the reduction process, there is no big loss in predictive accuracy and there can be an increase in accuracy.

TABLE 4

Effect of EP Reduction

| Dataset | #records | #attributes | # classes | CAEP Accuracy w/o red. | red. | #EPs/class w/o red. | Red. |
|---|---|---|---|---|---|---|---|
| Mushroom | 8124 | 22 | 2 | 98.82% | 98.93% | 823649 | 2738 |
| Rice-DNA | 15760 | 25 | 2 | 70.87% | 75.63% | 30555 | 24449 |
| Tic-tac-toe | 958 | 9 | 2 | 99.06% | 96.87% | 5707 | 682 |

TABLE 5

Precision and Sensitivity of CAEP

| Dataset | Class (instance dist.) | Sensitivity w/o red. | red. | Precision w/o red. | Red. |
|---|---|---|---|---|---|
| mushroom | edible (52%) | 99.43% | 99.61% | 98.32% | 98.46% |
| | poisonous (48%) | 98.16% | 98.35% | 99.38% | 99.34% |
| tic-tac-toe | positive (65%) | 99.52% | 96.01% | 99.07% | 99.21% |
| | negative (35%) | 98.19% | 98.49% | 99.13% | 93.12% |
| rice-DNA | positive (4%) | 77.01% | 73.91% | 9.58% | 10.95% |
| | negative (96%) | 70.62% | 75.70% | 98.71% | 98.63% |

The CAEP classifier uses almost no time to decide the class of an instance. Even for a classifier with 10000 EPs, the CAEP classifier takes only 0.01 second to decide the class label of an instance.

The rice-DNA dataset is quite different from datasets in the UCI repository. Reduction of EPs of either class leads to poor coverage of the training instances. This decision is made at training time.

Table 5 gives a more detailed characterization of CAEP on the datasets; sensitivity and precision on each class, before and after reduction, are listed. Table 5 shows that CAEP generally has good sensitivity and precision on each class.

The positive sensitivity and precision on the rice-DNA dataset are better than the best neural-net results known to us.

Thus, a classification method has been disclosed that is fundamentally different from previous classifiers, including C4.5 or CBA. This method is based on a new kind of knowledge mined from the training dataset: emerging patterns (EPs).

Specifically, the classifier CAEP is based on aggregating the contribution of all EPs for differentiating instances of different classes. The aggregate score is proposed to quantify the overall contribution of all the EPs. The contribution of an EP takes into account both the support and growth rate of the EP. The aggregate scores are normalized to classify instances, by dividing the scores by the base scores (chosen at a certain percentile of training instance scores) of the corresponding classes. The resulting classifier CAEP is in general more accurate than C4.5 and CBA, and is a lot more accurate than them over datasets where they do not have good performance. CAEP is equally accurate on all classes, and can be built efficiently from large, even high dimensional datasets. Observing that accuracy on the whole dataset is too coarse a description of classifiers, a more accurate measure, sensitivity and precision, is used to better characterize the performance of classifiers. CAEP also performs well under this measure.

9. Computer Implementation

Figure 2:
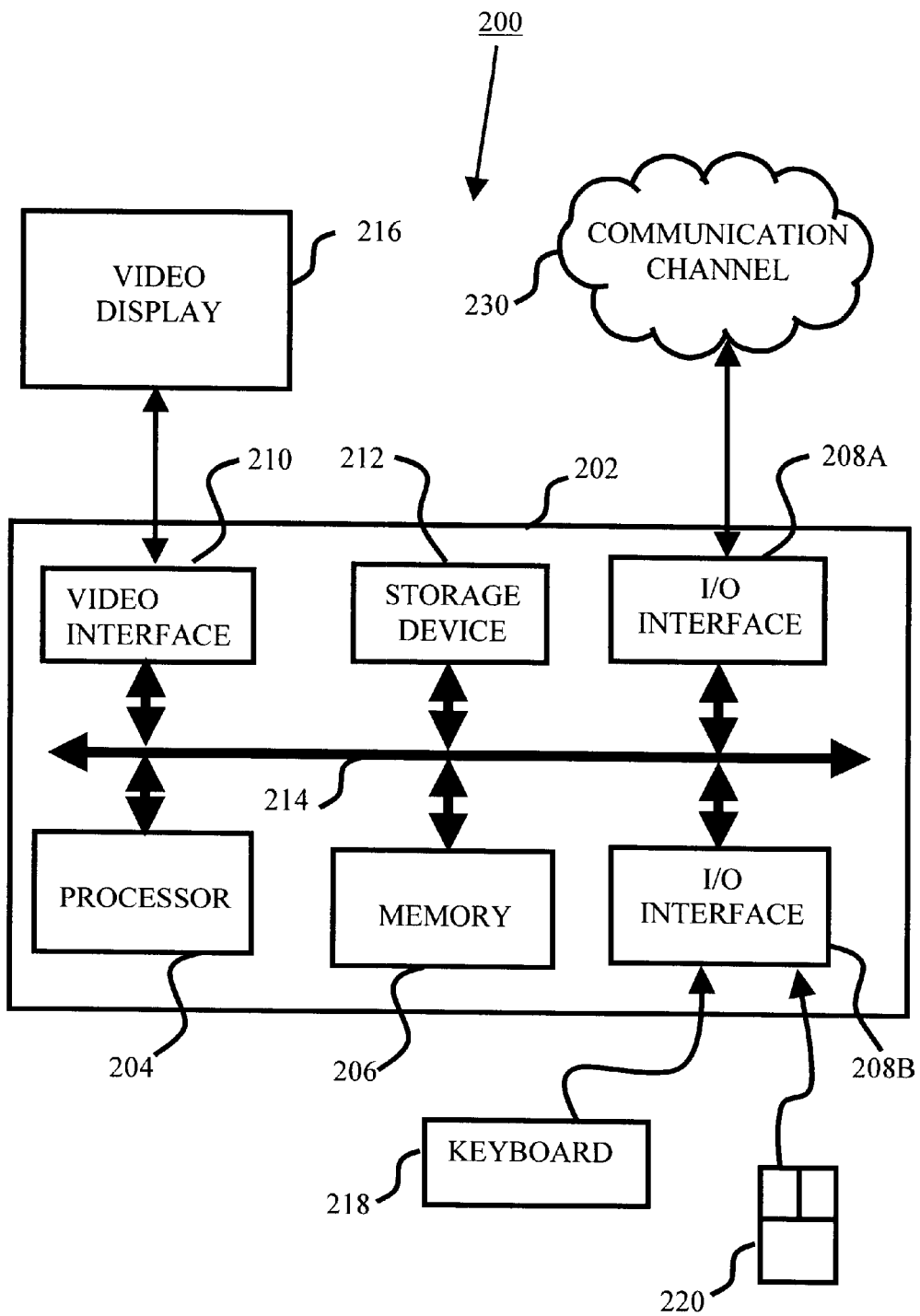
FIG. 2 is a block diagram of a general purpose computer with which the embodiments of the invention can be practiced.

The embodiments of the invention are preferably implemented using a computer, such as the general-purpose computer shown in FIG. 2. In particular, the process of FIG. 1 can be implemented as software, or a computer program, executing on the computer. The method or process steps for classification by aggregating EPs are effected by instructions in the software that are carried out by the computer. The software may be implemented as one or more modules for implementing the process steps. A module is a part of a computer program that usually performs a particular function or related functions. Also, a module can also be a packaged functional hardware unit for use with other components or modules.

In particular, the software may be stored in a computer readable medium, including the storage devices described below. The software is preferably loaded into the computer from the computer readable medium and then carried out by the computer. A computer program product includes a computer readable medium having such software or a computer program recorded on it that can be carried out by a computer. The use of the computer program product in the computer preferably effects an advantageous apparatus for classification by aggregating EPs in accordance with the embodiments of the invention.

The computer system 200 consists of the computer 202, a video display 216, and input devices 218, 220. In addition, the computer system 200 can have any of a number of other output devices including line printers, laser printers, plotters, and other reproduction devices connected to the computer 202. The computer system 200 can be connected to one or more other computers via a communication interface 208b using an appropriate communication channel 230 such as a modem communications path, a computer network, or the like. The computer network may include a local area network (LAN), a wide area network (WAN), an Intranet, and/or the Internet.

The computer 202 itself consists of a central processing unit(s) (simply referred to as a processor hereinafter) 204, a memory 206 which may include random access memory (RAM) and read-only memory (ROM), input/output (IO) interfaces 208A and 208B, a video interface 210, and one or more storage devices generally represented by a block 212 in FIG. 2. The storage device(s) 212 can consist of one or more of the following: a floppy disc, a hard disc drive, a magneto-optical disc drive, CD-ROM, magnetic tape or any other of a number of non-volatile storage devices well known to those skilled in the art. Each of the components 204 to 212 is typically connected to one or more of the other devices via a bus 214 that in turn can consist of data, address, and control buses. The video interface 210 is connected to the video display 216 and provides video signals from the computer 202 for display on the video display 216. User input to operate the computer 202 can be provided by one or more input devices 208b. For example, an operator can use the keyboard 218 and/or a pointing device such as the mouse 220 to provide input to the computer 202.

The system 200 is simply provided for illustrative purposes and other configurations can be employed without departing from the scope and spirit of the invention. Computers with which the embodiment can be practiced include IBM-PC/ATs or compatibles, one of the Macintosh (M family of PCs, Sun Sparcstation (TM, a workstation or the like. The foregoing are merely exemplary of the types of computers with which the embodiments of the invention may be practiced. Typically, the processes of the embodiments, described hereinafter, are resident as software or a program recorded on a hard disk drive (generally depicted as block 212 in FIG. 2) as the computer readable medium, and read and controlled using the processor 204. Intermediate storage of the program and pixel data and any data fetched from the network may be accomplished using the semiconductor memory 206, possibly in concert with the hard disk drive 212.

In some instances, the program may be supplied to the user encoded on a CD-ROM or a floppy disk (both generally depicted by block 212), or alternatively could be read by the user from the network via a modem device connected to the computer, for example. Still further, the software can also be loaded into the computer system 200 from other computer readable medium including magnetic tape, a ROM or integrated circuit, a magneto-optical disk, a radio or infra-red transmission channel between the computer and another device, a computer readable card such as a PCMCIA card, and the Internet and Intranets including email transmissions and information recorded on websites and the like. The foregoing are merely exemplary of relevant computer readable mediums. Other computer readable mediums may be practiced without departing from the scope and spirit of the invention.

Thus, a method, apparatus, and computer program product for classification of data by aggregating EPs have been described. While only a small number of embodiments are described, it will be apparent to those skilled in the art, in view of this disclosure, that numerous changes and/or modifications can be made without departing from the scope and spirit of the invention.

APPENDIX A

Extract of "Efficiently Mining Long Patterns from Databases"

*Proc of the* 1998 *ACM-SIGMOD Int'l Conf On Management of Data*, pp 85–93

Roberto J Bayardo Jr.

A data-set is a set of transactions that are sets over a finite domain of items. Transactions can represent things such as the supermarket items purchased by a customer during a shopping visit, or the characteristics of a person as described by his or her replies in a census questionnaire. A set of items is more succinctly called an itemset, and a frequent itemset is one that is contained in a number of transactions above or equal to the minimum support (minsup) specified by the user. An itemset with k items is more succinctly referred to as a k-itemset. The support of an itemset I, denoted sup(I), is the number of transactions that contain the itemset. The minsup parameter is sometimes specified as a percentage of the transactions in the data-set instead of as an absolute number of transactions.

Max-Miner can be described using a generic set-enumeration tree search framework. The idea is to expand sets over an ordered and finite item domain as illustrated in FIG. 3 below.

Figure 3:
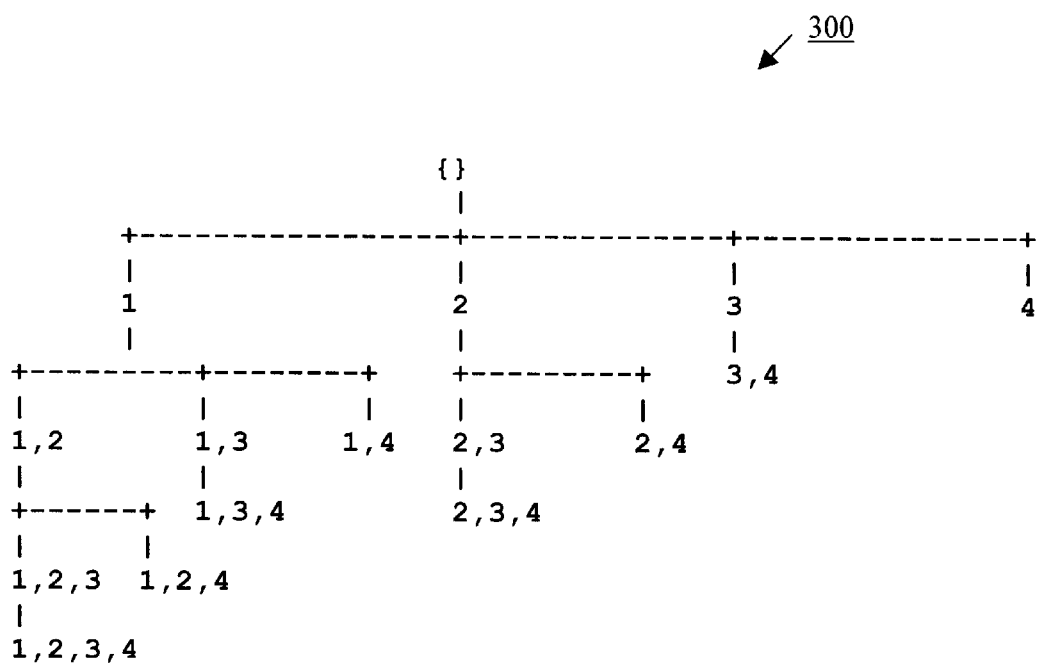
FIG. 3 illustrates a complete set-enumeration tee over four items.

In FIG. 3, the four items are denoted by their position in the ordering. The particular ordering imposed on the item domain affects the parent/child relationships in the set-enumeration tree 300 but not its completeness. Set-enumeration trees 300 are not data-structures like a hash tree or trie, but instead are used to illustrate how sets of items are to be completely enumerated in a search problem. Note that the tree could be traversed depth-first, breadth first, or even best-first as directed by some heuristic. Max-Miner employs a purely breadth-first search of the set-enumeration tree in order to limit the number of passes made over the data.

The key to an efficient set-enumeration search is the pruning strategies that are applied to remove entire branches from consideration. Without pruning, a set-enumeration tree search for frequent itemsets considers every itemset over the set of all items. Max-Miner uses pruning based on subset infrequency, also uses pruning based on superset frequency.

To aid in MaxMiner's pruning efforts, each node in the set enumeration tree is represented by a candidate group. A candidate group g consists of two itemsets. The first, called the head and denoted h(g), represents the itemset enumerated by the node. The second itemset, called the tail and denoted t(g), is an ordered set and contains all items not in h(g) that can potentially appear in any sub-node. For example, the node enumerating itemset {1} in the figure has h(g)={1} and t(g)={2, 3, 4}. The ordering of tail items reflect how the subnodes are to be expanded. In the case of a static lexical ordering without pruning, the tail of any candidate group is trivially the set of all items following the greatest item in the head according to the item ordering. As Maxminer uses pruning, it becomes necessary to make the tail items explicit.

MaxMiner computes the support of itemsets h(g), h(g) ∪t(g), and h(g) ∪{i} for all i in t(g). The supports of itemsets other than h(g) are used for pruning. For example, consider first the itemset h(g) ∪t(g). Since h(g) ∪t(g) contains every item that appears in any viable sub-node of g, if it is frequent, then any itemset enumerated by a sub-node will also be frequent but not maximal. Superset-frequency pruning is thus implemented in MaxMiner by halting sub-node expansion at any candidate group g for which h(g) ∪t(g) is frequent.

Consider next the itemset h(g) ∪{i} for some i in t(g). if h(g) u {i} is infrequent, then any head of a sub-node that contains item i is also infrequent. Subset infrequency pruning is thus implemented in MaxMiner by simply removing any such tail item from a candidate group before expanding its sub-nodes.

APPENDIX B

Border-Based Mining of Emerging Patterns

A collection S of sets is called interval closed if, for all X, Z ∈S and for all Y, it is the case that Y ∈S whenever X⊆Y $\subseteq Z$ For example, $S=\{\{1, 2\}, \{2, 3\}, \{1, 2, 3\}, \{1, 2, 4\}, \{2, 3, 4\}, \{1, 2, 3, 4\}\}$ is interval-closed. The collection of all large itemsets with respect to any fixed threshold (i.e., itemsets having supports that are larger than the threshold) is interval closed Borders offer succinct representation of such collections, which are typically quite large.

An ordered pair <L, R> is called a border, L is the left-hand bound of this border, and R is the right-hand bound, if (a) each of L and R is an antichain collection of sets, and (b) each element of L is a subset of some element in R and each element of R is a superset of some element in L.

A collection S of sets is an antichain if X and Y are incomparable sets (i.e. $X \not\subseteq Y$ and $Y \not\subseteq X$) for all X, Y $\in$ S. The collection of sets represented by, or the set interval of, a border <L, R>, is $[L,R]=\{Y | \exists X \in L, \exists Z \in R \text{ such that } X \subseteq Y \subseteq Z\}$. The collection [L,R] is said to have <L,R>as border.

The set interval of $<\{\{1\}, \{2, 3\}1\}, \{\{1, 2, 3\}, \{2, 3, 4\}\}>$ is $\{\{1\}, \{1, 2\}, \{1, 3\} \{1, 2, 3\} \{2, 3\} \{2, 3, 4\}\}$. The set interval of $<\{\{1, 2\}\}, \{\{1, 2, 3, 4, 5\}, \{1, 2, 4, 5, 6\}\}>$ consists of 12 itemsets: all sets that are both supersets of $\{1, 21\}$ and subsets of either $\{1, 2, 3, 4, 5\}$ or $\{1, 2, 4, 5, 6\}$. Many simple borders' set intervals are large collections; e.g. there are $2^{11}$ itemsets in the set interval of $<\{\{1\}\}, \{\{1, 2, 3, 4, 5, 6, 7, 8, 9, 10, 11, 12\}\}>$.

There is a one-to-one correspondence between borders and interval-closed collections: Each interval-closed collection S of sets has a unique border <As R>, where L is the collection of minimal sets in S, and R is the collection of maximal sets in S. The border-based processes can discover all EPs satisfying a certain support constraint and do this without enumerating elements of large collections. In fact, the entire process of discovering EPs in this rectangle only needs to deal with borders: the border-based processes takes borders, which represent collections of large itemsets, as inputs; the border-based processes only manipulates borders in the internal process; and the border-based processes produce as output borders that represent EPs. Consequently, the running time of this process is short for most practical situations, even when the number of EPs is huge.

Discussion is concentrated on the situation when two large borders, one from $D_1$ and another from $D_2$, are available. The differential procedure, called BORDER-DWF, is given first. Then the main process, MBDLLBORDER, using BORDER-DIFF as a subroutine, is given.

BORDER-DIFF aims to derive the differential between a pair of borders with a special form: given a pair of borders $<\{\emptyset\}, \{U\}>$ and $<\{\emptyset\}, R_1>$, BORDER-DIFF derives another border $<L_2, \{U\}>$ such that $[L_2, \{U\}]=[\{\emptyset\}, \{U\}]-[\{\emptyset\}, R_1]$.

BORDER-DIFF($<\{\emptyset\},\{U\}>, <\{\emptyset\}, \{S_1, S_2, \ldots, S_k\}>$)

;; improved version

;; return border of $[\{\emptyset\}, \{U\}]-[\{\emptyset\}, \{S_1, S_2, \ldots, S_k\}]$ 1) initialize L to $\{\{x\}|x \in U-S_1\}$;
2) for i=2 to k do
3) $L \leftarrow \{X \cup \{x\} | X \in L, x \in U-S_i\}$;
4) remove all Y in L that are not minimal;
5) rerun <L, $\{U\}$>.

Operation of the BORDER-DIFF process is illustrated using the arguments of $<\{\emptyset\}, \{1, 2, 3, 4\}>$ and $<\{\emptyset\}, \{3, 4\}, \{2, 4\}, \{2, 3\}\}>$. The process first initializes L to $\{\{1\}, \{2\}\}$ since $U-S_1=\{1, 2\}$. Then the process updates L to $\{\{1\}, \{1, 2\}, \{1, 3\}, \{2, 3\}\}$ since $U-S_2=\{1, 3\}$, and reduces it to $\{\{1\}, \{2, 3\}\}$. Finally the process updates L to $\{\{1\}, \{1, 2, 3\}, \{1, 4\}, \{2, 3, 4\}\}$ since $U-S_3=\{1, 4\}$, and reduces it to $\{\{1\}, \{2, 3, 4\}\}$.

Assuming that LARGEBORDER$_\delta(D_1^*)=<\{\emptyset\}, \{C_1, C_2, \ldots C_M\}>$ (which represents all $\delta$-large itemsets from $D_1^*$) and LARGEBORDER$_\theta(D_2^*)=<\{\emptyset\}, \{D_1, D_2, \ldots, D_n\}>$ have been found for some $\delta$ and $\theta$ satisfying $\theta=p^*\delta$. The MBD-LLBORDER process finds all EPs satisfying: their supports in $D_2^*$ are $\geq \delta^* \rho$ but their supports in $D_1$ are $<\delta$.

MBD-LLBORDER (LARGEBORDER$_\delta(D_1^*)$, LARGEBORDER$_{\{s2\}\theta(D2}^*))$

;; return all emerging patterns satisfying (*) by multiple calls of BORDER-DIFF

1) EPborders$\leftarrow\{\}$;
2) for j from 1 to n do
3) if some $C_i$ is a superset of $D_j$ then continue;
4) $\{C'_1, \ldots, C'_m\} \leftarrow \{C_1 \cap D_j, \ldots, C_m \cap D_j\}$;
5) RightBound$\leftarrow$set of all maximal itemsets in $\{C'_1, \ldots, C'_m\}$;
6) add BORDER-DFF($<\{\theta\}, D_j>, <\{\emptyset\}$, RightBound>) into EPborders;
7) return EPborders;

Operation of the MBD-LLBORDER is now illustrated for:

LargeBorder$_\delta(D_1)=<\{\emptyset\}, \{\{2, 3, 5\}, \{3, 4, 6, 7, 8\}, \{2, 4, 5, 8, 9\}\}>$ LargeBorder$_\theta(D_2)=<\{\emptyset\}, \{\{1, 2, 3, 4\}, \{6, 7, 8\}>$.

For $D_1=\{1, 2, 3, 4\}$, $C_1=\{2, 3, 5\}$, $C_2=\{3, 4, 6, 7, 8\}$, $C_3=\{2, 4, 5, 8, 9\}$, step 4 of the MBD-LLBORDER process produces $C'_1=\{2, 3\}$, $C'_2=\{3, 4\}$, $C'_3=\{2, 4\}$; the process then calls BORDER-DIFF with $<\{\emptyset\}, \{\{1, 2, 3, 4\}\}>$ and $<\{\emptyset\}, \{\{2, 3\}, \{3, 4\}, \{2, 4\}\}$, since Cs are all minimal. The BORDER-DW process then returns $<\{\{1\}, \{2, 3, 4\}\}, \{\{1, 2, 3, 4\}\}>$. Since $\{6, 7, 8\} \subseteq \{3, 4, 6, 7, 8\}=D_2$, the UMD-LLBORDER process does not call BORDER-DIFF for $D_2$ since the answer is known to be empty.

What is claimed is:

1. A method of classifying data by aggregating emerging patterns in said data using datasets for a plurality of classes using a computer processor, said method including the steps of:

for each of said classes, mining an emerging pattern set dependent upon instances of said set and opponent instances dependent upon predetermined growth rate and support thresholds;

calculating aggregate scores of said instances for all of said classes;

determining base scores for each of said classes; and for each test instance, performing the sub-steps of:

calculating aggregate and normalised scores of test instance for each class; and assigning a specified class to the test instance for which the test instance has a largest normalized score;

wherein said mining step includes the steps of:

determining borders of large itemsets using a largeborder based technique; and determining supports and growth rates of emerging patterns for said class.

2. The method according to claim 1, further including the step of reducing the number of emerging patterns dependent upon growth rates and supports of said emerging patterns.

3. The method according to claim 1, further including the step of partitioning an original dataset into a predetermined number of datasets to form said datasets, the predetermined number of datasets dependent upon the number of classes.

4. The method according to claim 1, wherein said largeborder based technique is the Max-Miner technique.

5. An apparatus having a computer processor for classifying data by aggregating emerging patterns in said data using datasets for a plurality of classes, said apparatus including:
 means for, for each of said classes, mining an emerging pattern set dependent upon instances of said set and opponent instances dependent upon predetermined growth rate and support thresholds;
 means for calculating aggregate scores of said instances for all of said classes;
 means for determining base scores for each of said classes; and
 means for, for each test instance, performing specified operations, said performing means including:
  means for calculating aggregate and normalised scores of test instance for each class; and
  means for assigning a specified class to the test instance for which the test instance has a largest normalized score;
 wherein said mining means includes:
  means for determining two large borders of instances of said set and of said opponent set; and
  means for finding all emerging pattern borders using multiple border pairs.

6. A method of classifying data by aggregating emerging patterns in said data using datasets for a plurality of classes using a computer processor, said method including the steps of:
 for each of said classes, mining an emerging pattern set dependent upon instances of said set and opponent instances dependent upon predetermined growth rate and support thresholds;
 calculating aggregate scores of said instances for all of said classes;
 determining base scores for each of said classes; and
 for each test instance, performing the sub-steps of:
  calculating aggregate and normalised scores of test instance for each class; and
  assigning a specified class to the test instance for which the test instance has a largest normalized score;
 wherein said mining step includes the steps of:
  determining two large borders of instances of said set and of said opponent set; and
  finding all emerging pattern borders using multiple border pairs.

7. An apparatus having a computer processor for classifying data by aggregating emerging patterns in said data using datasets for a plurality of classes, said apparatus including:
 means for, for each of said classes, mining an emerging pattern set dependent upon instances of said set and opponent instances dependent upon predetermined growth rate and support thresholds;
 means for calculating aggregate scores of said instances for all of said classes;
 means for determining base scores for each of said classes; and
 means for, for each test instance, performing specified operations, said performing means including:
  means for calculating aggregate and normalised scores of test instance for each class; and
  means for assigning a specified class to the test instance for which the test instance has a largest normalized score;
 wherein said mining means further includes:
  means for determining borders of large itemsets using a large-border based technique; and
  means for determining supports and growth rates of emerging patterns for said class.

8. The apparatus according to claim 7, further including means for reducing the number of emerging patterns dependent upon growth rates and supports of said emerging patterns.

9. The apparatus according to claim 7, further including means for partitioning an original dataset into a predetermined number of datasets to form said datasets, the predetermined number of datasets dependent upon the number of classes.

10. The apparatus according to claim 7, wherein said large-border based technique is the Max-Miner technique.

11. A system for classifying data using a processor, said system including:
 means for inputting samples of said data to be classified;
 means for mining emerging patterns for all of a number of categories of said data;
 means for computing aggregate differentiating scores for all samples of said data and said categories;
 means for computing base scores of aggregate differentiating scores for all samples and categories; and
 means for assigning a category to each sample, said category assigned to a sample having a normalized score that is maximal for said sample;
 wherein said mining means includes;
  means for determining two large borders of large itemsets in two categories having predetermined support thresholds;
  means for finding emerging pattern borders using MBD-LLBORDER processing;
  means for enumerating emerging patterns contained in found emerging pattern borders; and
  means for checking through actual supports and growth rates of samples in said two categories.

12. A system for ranking and classifying data using a processor, said system including:
 means for inputting samples of said data to be classified;
 means for mining emerging patterns for all of a number of categories of said data;
 means for computing aggregate differentiating scores for all samples of said data and said categories;
 means for computing base scores of aggregate differentiating scores for all samples and categories; and
 means for ranking each category against each sample by measuring a normalized score for said sample, where the greater a normalized score, the higher is the rank of said sample, said normalized score formed by dividing said aggregate differentiating score by a corresponding base score;
 wherein said mining means includes;
  means for determining two large borders of large itemsets in two categories having predetermined support thresholds;
  means for finding emerging pattern borders using MBD-LLBORDER processing;
  means for enumerating emerging patterns contained in found emerging pattern borders; and
  means for checking through actual supports and growth rates of samples in said two categories.

13. A computer program product having a computer readable medium having a computer program recorded therein for classifying data by aggregating emerging patterns in said data using datasets for a plurality of classes, said computer program product including:
    computer program source code means for, for each of said classes, mining an emerging pattern set dependent upon instances of said set and opponent instances dependent upon predetermined growth rate and support thresholds;
    computer program source code means for calculating aggregate scores of said instances for all of said classes;
    computer program source code means for determining base scores for each of said classes; and
    computer program source code means for, for each test instance, performing specified operations, said computer program source code performing means including:
        computer program source code means for calculating aggregate and normalised scores of test instance for each class; and
        computer program source code means for assigning a specified class to the test instance for which the test instance has a largest normalized score;
    wherein said computer program source code mining means further includes:
        computer program source code means for determining borders of large itemsets using a large-border based technique; and
        computer program source code means for determining supports and growth rates of emerging patterns for said class.

14. The computer program product according to claim 13, further including computer program source code means for reducing the number of emerging patterns dependent upon growth rates and supports of said emerging patterns.

15. The computer program product according to claim 13, further including computer program source code means for partitioning an original dataset into a predetermined number of datasets to form said datasets, the predetermined number of datasets dependent upon the number of classes.

16. The computer program product according to claim 13, wherein said large-border based technique is the Max-Miner technique.

17. A system for extracting emerging patterns from data using a processor, said system including:
    means for mining emerging patterns for all of a number of categories of said data;
    means for computing aggregate differentiating scores for all samples of said data and said categories; and
    means for computing base scores for said categories;
    wherein said mining means includes;
        means for determining two large borders of large itemsets in two categories having predetermined support thresholds;
        means for finding emerging pattern borders using MBD-LLBORDER processing;
        means for enumerating emerging patterns contained in found emerging pattern borders; and
        means for checking through actual supports and growth rates of samples in said two categories.

18. A computer program product having a computer readable medium having a computer program recorded therein for classifying data by aggregating emerging patterns in said data using datasets for a plurality of classes, said computer program product including:
    computer program source code means for, for each of said classes, mining an emerging pattern set dependent upon instances of said set and opponent instances dependent upon predetermined growth rate and support thresholds;
    computer program source code means for calculating aggregate scores of said instances for all of said classes;
    computer program source code means for determining base scores for each of said classes; and
    computer program source code means for, for each test instance, performing specified operations, said computer program source code performing means including:
        computer program source code means for calculating aggregate and normalised scores of test instance for each class; and
        computer program source code means for assigning a specified class to the test instance for which the test instance has a largest normalized score;
    wherein said computer program source code mining means includes:
        computer program source code means for determining two large borders of instances of said set and of said opponent set; and
        computer program source code means for finding all emerging pattern borders using multiple border pairs.

19. A system for extracting emerging patterns from data using a processor, said system including:
    means for mining emerging patterns for all of a number of categories of said data;
    means for computing aggregate differentiating scores for all samples of said data and said categories; and
    means for computing base scores for said categories;
    wherein said mining means includes means for manipulating borders, where each border is an ordered pair (L, R), if each of L and R is an anti-chain collection of sets, each element of L is a subset of an element of R, and each element of R is a superset of some element in L, wherein a collection of sets represented by, or a set interval of, such a border are sets Y such that Y is a superset of an element of L and is a subset of an element of R.

20. The system according to claim 19, further including means for extracting said emerging patterns from said mined emerging patterns dependent upon said aggregated differentiating scores and said base scores.

21. The system according to claim 19, further including means for reducing the number of related emerging patterns, two emerging patterns being related if one is a sub-pattern or subset of the other.

22. The system according to claim 21, further including means for indicating whether the set of derived emerging patterns is to be reduced, operations of said reducing means being dependent upon said indicating means.

23. The system according to claim 19, further including means for reproducing in a displayable manner extracted emerging patterns.

24. The system according to claim 19, further including:
    means for obtaining samples from different input categories; and
    means for adjustably discretizing said obtained samples.

25. The system according to claim 19, further including means for storing and managing said obtained samples and/or said discretized samples.

26. The system according to claim 19, wherein said emerging patterns are derived dependent upon one or more predetermined conditions include:

a support level threshold of a pattern in a category;

a growth rate threshold between categories;

a monotonically increasing weighting function for a growth rate;

a score specifying an aggregate differentiating score of a discretized sample and a set of emerging patterns of a category, said score being dependent upon supports and weighted growth rates of emerging patterns in a category; and a base score on said aggregate differentiating score for each category.

27. The system according to claim 26, further including means for storing and managing derived emerging patterns and said one or more conditions for deriving said emerging patterns.

28. The system according to claim 19, further including means for selecting patterns that cover more training samples and have stronger differentiating power, said pattern selecting means including:

means for sorting emerging patterns between two categories into a list in decreasing order of growth rate and support;

means for initializing a set of essential emerging patterns, essE, to contain a first emerging pattern in said list; and means for, for each next pattern in said list, ordering said set of essential emerging patterns, said ordering means including:

means for, for each J in said set of emerging patterns essE such that I is a sub-pattern or subset of J, replacing J by I if either of the following conditions is true:

growthrate $_{C' \to C}(I)$ exceeds growthrate $_{C' \to C}(J)$, $supp_c(I)$ greatly exceeds $supp_c(J)$ and growthrate $_{C' \to C}(I)$ exceeds the threshold on growth rate; and means for adding I to said set of emerging patterns essE if both of the above conditions are false and I is not a super-pattern or superset of any pattern in said set of emerging patterns essE.

29. A system for ranking and classifying data using a processor, said system including:

means for inputting samples of said data to be classified;

means for mining emerging patterns for all of a number of categories of said data;

means for computing aggregate differentiating scores for all samples of said data and said categories;

means for computing base scores of aggregate differentiating scores for all samples and categories; and means for ranking each category against each sample by measuring a normalized score for said sample, where the greater a normalized score, the higher is the rank of said sample, said normalized score formed by dividing said aggregate differentiating score by a corresponding base score;

wherein said mining means includes means for manipulating borders, where each border is an ordered pair (L, R), if each of L and R is an anti-chain collection of sets, each element of L is a subset of an element of R, and each element of R is a superset of some element in L, wherein a collection of sets represented by, or a set interval of, such a border are sets Y such that Y is a superset of an element of L and is a subset of an element of R.

30. The system according to claim 29, further including means for outputting ranked classification decisions on said samples.

31. A system for classifying data using a processor, said system including:

means for inputting samples of said data to be classified;

means for mining emerging patterns for all of a number of categories of said data;

means for computing aggregate differentiating scores for all samples of said data and said categories;

means for computing base scores of aggregate differentiating scores for all samples and categories; and means for assigning a category to each sample, said category assigned to a sample having a normalized score that is maximal for said sample;

wherein said mining means includes means for manipulating borders, where each border is an ordered pair (L, R), if each of L and R is an anti-chain collection of sets, each element of L is a subset of an element of R, and each element of R is a superset of some element in L, wherein a collection of sets represented by, or a set interval of, such a border are sets Y such that Y is a superset of an element of L and is a subset of an element of R.

32. The system according to claim 31, further including means for outputtng classification decisions on said samples.

* * * * *